United States Patent [19]
Gitter et al.

[11] Patent Number: 5,525,624
[45] Date of Patent: Jun. 11, 1996

[54] NON-PEPTIDE TACHYKININ RECEPTOR ANTAGONISTS TO TREAT PSYCOLOGICAL DISORDER

[75] Inventors: Bruce D. Gitter, Carmel; William H. W. Lunn, Indianapolis, both of Ind.

[73] Assignee: Eli Lilly and Company, Indianapolis, Ind.

[21] Appl. No.: 403,969

[22] Filed: Mar. 15, 1995

Related U.S. Application Data

[63] Continuation of Ser. No. 168,484, Dec. 21, 1993.

[51] Int. Cl.$^6$ ..................................................... A61K 31/38
[52] U.S. Cl. ..................................................... 514/443
[58] Field of Search ..................................................... 514/443

[56] References Cited

U.S. PATENT DOCUMENTS

| 4,133,814 | 1/1979 | Jones et al. | 260/326.55 |
| 4,380,635 | 4/1983 | Peters | 546/202 |
| 4,418,068 | 11/1983 | Jones | 424/267 |

FOREIGN PATENT DOCUMENTS

| WO93/10113 | 5/1993 | Japan. |
| WO93/1074 | 6/1993 | WIPO. |

OTHER PUBLICATIONS

Draper et al., "Effects of Raloxifene (LY139481 HC1) on Biochemical Markers of Bone and Lipid Metabolism i Healthy Postmenopausal Women", Hong Kong, Fourth Int'l Symp. on Osteoporosis, Mar. 29, 1993.
Bryant et al., "Protection from Bone Loss and Lowering of Serum Cholesterol in the Absence of Uterine Stimulation in Overiectomized Rats", Am Soc. Bone & Min. Res., Tampa, Sep. 18–22, 1993.
Bryant et al., "Raloxifene is a Tissue Specific Estrogen Agonist", Am Soc. Bone & Min. Res., Tampa, Sep. 18–22, 1993.
Frolick et al., "In Vivo and In Vitro Metabolism of Raloxifene", Am. Soc. Bone & Min. Res., Tampa, Sep. 18–22, 1993.
Glasebrook et al., "Multiple Binding Sites for the Anti-estrogen Raloxifene", Am Soc. Bone & Min. Res., Tampa, Sep. 18–22, 1993.
Hock et al., "Combination of Raloxifene and Human Parathyoid Hormone 1–34; Increased Femur Bone Mass in Young Overiectomized (OVX) Rats", Am. Soc. Bone & Min. Res., Tampa, Sep. 18–22, 1993.
Sato et al., "DEXA Analysis of Raloxifene Effects on the Bones From Ovariectomized Rats", Am. Soc. for Bone and Min. Res., Tampa, Sep. 18–22, 1993.
Yang et al., "Raloxifene an Anti-Estrogen, Simulates the Effects of Estrogen in Inhibiting Bone Resorption through Regulating TGFB-3 Expression in Bone; " .Am Soc. for Bone and Min. Res., Tampa, Sep. 18–22, 1993.

Black et al., "Distinct, Structures–Related Profiles of Estrogenic and Anti-Estrogenic Activity in the Tamoxifen and LY117018 Series; " The Endocrine Society, Abstract 1982.
Black et al., "Uterine Bioassay of Tamoxifen, Trioxifen, and New Estrogen Antagonist (LY117018) in Rats and Mice," Life Sciences, 26:1980, 1453–1458.
Black et al., "Differential Interaction of Antiestrogens with Cytosol Estrogen Receptors, " Molecular and Cellular Endocrinology, 22:1981, 95–103.
Black et al., "Evidence for Biological Action of the Antiestrogens LY117018 and Tamoxifen by Different Mechanisms," Endocrinology 109;1981, 987–989.
Black, L. J. "Biological Actions and Binding Properties of a New Estrogen Antagosist LY117018," In: Homone Antagonists, 129–82, 1982 (M. K. Agarwal ed.) Walter de Gruyter and Co., Berlin New York.
Black et al., LY156758: A Unique Antiestrogen Displaying High Affinity for Estrogen Receptors, Negligible Estrogenic Activity and Near-Total Estrogen Antagonism in Vivo. Presented at the Fifth Annual San Antonio Breast Cancer Symposium, San Antonio, Texas, Nov. 5–6, 1982.
Black et al., The Antiestrogenic Action of LY139481: Species Uniformity Duration of Action and Kinetics of 3H-Ly139481 Distribution In Vivo. Sixty–fifth Annual Meeting of the Endocrine Society, San Antonio Texas, Jun. 8–10, 1983, abs. 93.
Black et al., Antagonism of Estrogen Action with a New benzothiopene Derived Antiestrogen, Life Sciences, 32:1983. 1031–1036.

(List continued on next page.)

Primary Examiner—Theodore J. Criares
Attorney, Agent, or Firm—James J. Sales

[57] ABSTRACT

This invention encompasses methods for the treatment or prevention of a physiological disorder associated with an excess of tachykinins, which method comprises administering to a mammal in need of said treatment an effective amount of a compound of Formula I

[Chemical structure of Formula I showing a benzothiophene core with $R^1O$ substituent, phenyl group with $OR^3$ substituent, and carbonyl-linked phenyl with $OCH_2CH_2-R^2$ substituent]

wherein $R^1$ and $R^3$ are independently hydrogen, $-CH_3$, $-\overset{O}{\underset{\|}{C}}-(C_1-C_6\text{alkyl})$, or $-\overset{O}{\underset{\|}{C}}-Ar$, wherein Ar is optionally substituted phenyl;
$R^2$ is selected from the group consisting of pyrrolidine, hexamthylenemino, and piperidino; or a pharmaceutically acceptable salt of solvate thereof.

4 Claims, No Drawings

OTHER PUBLICATIONS

Black et al., The Relationship of the Antiestrogenic Efficacy of LY156758 to its Pharmacokinetics and Metabolism Following Oral Administration to Adult Ovariectomized Rats, Seventh International Congress of Endocrinology, Quebec City, Canada, Jul. 1–7, 1984, abs. 323.

Black et al., Synthesis and Antiestrogenic Activity of [3,4–Dihydro–2 (4–methoxyphenyl)–1–napthalenyl] [4–[2–pyrrolidinyl) ethoxyl]–phenyl] methanone, methanesulfonic acid salt, Journal of Medicinal Chemistry 22;1979, 962–966.

Black et al., Antiestrogens 2. Structure Activity Studies in a Series of 3-Aroyl-2-arylbenzo [b]thiophene Derivatives Leading to [6-Hydroxy-2-(4-hydroxyphenyl) benzo [b]thien-3-yl] [4-[2-(1-[6-Hydroxy-2-(4-hydroxyphenyl) benzo [b]thien-3-yl] [4-[2-(1-picridinyl) ethoxy]-phenyl]methanone Hydrochloride (LY156758), a Remarkably Effective Estrogen Antagonist with Only Minimal Intrinsic Estrogenicity, J. Med. Chem. 27(8), 1984, 1057–1066.

NON-PEPTIDE TACHYKININ RECEPTOR ANTAGONISTS TO TREAT PSYCOLOGICAL DISORDER

This application is a continuation of application Ser. No. 08/168,484, filed Dec. 21, 1993, pending.

BACKGROUND OF THE INVENTION

Tachykinins are a family of peptides which share the common amidated carboxy terminal sequence,

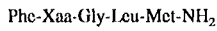

hereinafter referred to as SEQ ID NO:1. Substance P was the first peptide of this family to be isolated, although its purification and the determination of its primary sequence did not occur until the early 1970's. Substance P has the following amino acid sequence,

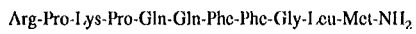

hereinafter referred to as SEQ ID NO:2.

Between 1983 and 1984 several groups reported the isolation of two novel mammalian tachykinins, now termed neurokinin A (also known as substance K, neuromedin L, and neurokinin α), and neurokinin B (also known as neuromedin K and neurokinin β). See, J. E. Maggio, *Peptides*, 6 (Supplement 3):237–243 (1985) for a review of these discoveries. Neurokinin A has the following amino acid sequence,

hereinafter referred to as SEQ ID NO:3. The structure of neurokinin B is the amino acid sequence,

hereinafter referred to as SEQ ID NO:4.

Tachykinins are widely distributed in both the central and peripheral nervous systems, are released from nerves, and exert a variety of biological actions, which, in most cases, depend upon activation of specific receptors expressed on the membrane of target cells. Tachykinins are also produced by a number of non-neural tissues.

The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins or inappropriate stimulation of tachykinin receptors, the development of tachykinin receptor antagonists will serve to control these clinical conditions. The earliest tachykinin receptor antagonists were peptide derivatives. These antagonists proved to be of limited pharmaceutical utility because of their metabolic instability.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

SUMMARY OF THE INVENTION

This invention encompasses methods for the inhibition of a physiological disorder associated with an excess of tachykinins, which method comprises administering to a mammal in need thereof an effective amount of a compound of Formula I

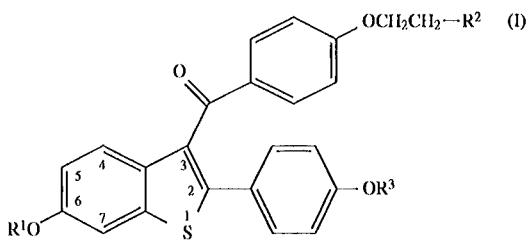

wherein $R^1$ and $R^3$ are independently hydrogen,

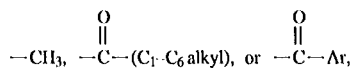

wherein Ar is optionally substituted phenyl;
$R^2$ is selected from the group consisting of pyrrolidino, hexamethylenemino, and piperidino; or a pharmaceutically acceptable salt of solvate thereof.

DETAILED DESCRIPTION OF THE INVENTION

The current invention concerns the discovery that a select group of benzothiophenes, those of formula I, are useful as tachykinin receptor antagonists. The invention encompasses uses practiced by administering to a mammal or human in need thereof a dose of a compound of formula 1 or a pharmaceutically acceptable salt or solvate thereof effective to inhibit a physiological disorder associated with an excess of tachykinins. The term inhibit includes its generally accepted meaning which includes prophylactic administration to a mammal or human subject to incurring a disorder described herein, and holding in check and/or treating existing disorders. As such, the methods include both therapeutic and prophylactic administration.

Generally, the compound is formulated with common excipients, diluents or carriers, and compressed into tablets, or formulated as elixirs or solutions for convenient oral administration, or administered by the intramuscular or intravenous routes. The compounds can be administered transdermally, and may be formulated as sustained release dosage forms and the like.

The compounds used in the methods of the current invention can be made according to established and analogous procedures, such as those detailed in U.S. Pat. Nos. 4,133,814, 4,418,068, and 4,380,635 all of which are incorporated by reference herein. In general, the process starts with a benzo[b]thiophene having a 6-hydroxyl group and a 2-(4-hydroxyphenyl) group. The starting compound is protected, alkylated, and deprotected to form the formula I compounds. Examples of the preparation of such compounds are provided in the U.S. patents discussed above, and in the examples in this application. Optionally substituted phenyl includes phenyl and phenyl substituted once or twice with $C_1$–$C_6$ alkyl, $C_1$–$C_4$ alkoxy, hydroxy, nitro, chloro, fluoro, or tri(chloro or fluoro)methyl.

Included in this invention is the compound raloxifene, below:

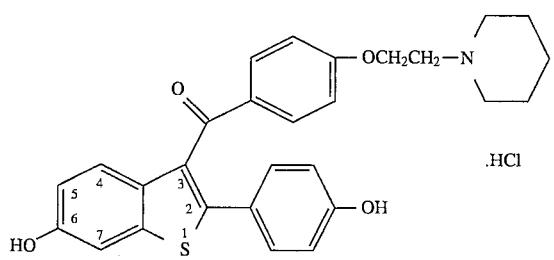

The compounds used in the methods of this invention form pharmaceutically acceptable acid and base addition salts with a wide variety of organic and inorganic acids and bases and include the physiologically acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, teraphthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzenesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like. A preferable salt is the hydrochloride salt.

The pharmaceutically acceptable acid addition salts are typically formed by reacting a compound of formula I with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides and carbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need of treatment from once to about three times each day, or more often as needed.

It is usually preferred to administer a compound of formula I in the form of an acid addition salt, as is customary in the administration of pharmaceuticals bearing a basic group, such as the piperidino ring. For such purposes the following dosage forms are available.

Formulations

In the formulations which follow, "Active ingredient" means a compound of formula I.

Formulation 1: Gelatin Capsules

Hard gelatin capsules are prepared using the following:

| Ingredient | Quantity (mg/capsule) |
|---|---|
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Examples of specific capsule formulations of the compound raloxifene that have been made include those shown below:

Formulation 2: Raloxifene capsule

| Ingredient | Quantity (mg/capsule) |
| --- | --- |
| Raloxifene | 1 |
| Starch, NF | 112 |
| Starch flowable powder | 225.3 |
| Silicone fluid 350 centistokes | 1.7 |

Formulation 3: Raloxifene capsule

| Ingredient | Quantity (mg/capsule) |
| --- | --- |
| Raloxifene | 5 |
| Starch, NF | 108 |
| Starch flowable powder | 225.3 |
| Silicone fluid 350 centistokes | 1.7 |

Formulation 4: Raloxifene capsule

| Ingredient | Quantity (mg/capsule) |
| --- | --- |
| Raloxifene | 10 |
| Starch, NF | 103 |
| Starch flowable powder | 225.3 |
| Silicone fluid 350 centistokes | 1.7 |

Formulation 5: Raloxifene capsule

| Ingredient | Quantity (mg/capsule) |
| --- | --- |
| Raloxifene | 50 |
| Starch, NF | 150 |
| Starch flowable powder | 397 |
| Silicone fluid 350 centistokes | 3.0 |

The specific formulations above may be changed in compliance with the reasonable variations provided.

A tablet formulation is prepared using the ingredients below:

Formulation 6: Tablets

| Ingredient | Quantity (mg/capsule) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 7: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 8: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

The biological activity of the compounds of the present invention are evaluated employing an initial screening assay which rapidly and accurately measures the binding of the tested compound to known NK-1 receptor sites. Assays useful for evaluating tachykinin receptor antagonists are well known in the art. See, e.g., J. Jukic, et al., *Life Sciences*, 49:1463–1469 (1991); N. Kucharczyk, et al., *Journal of Medicinal Chemistry*, 36:1654–1661 (1993); N. Rouissi, et al., *Biochemical and Biophysical Research Communications* 176:894–901 (1991).

NK-1 Receptor Binding Assay

Radioreceptor binding assays are performed using a derivative of a previously published protocol. D. G. Payan, et al., *Journal of Immunology*, 133:3260–3265 (1984). In this assay an aliquot of IM9 cells ($1 \times 10^6$ cells/tube in RPMI 1640 medium supplemented with 10% fetal calf serum) is incubated with 20 pM $^{125}$I-labeled substance P in the presence of increasing competitor concentrations for 45 minutes at 4° C.

The IM9 cell line is a well-characterized and readily available human cell line. See, e.g., *Annals of the New York Academy of Science*, 190:221–234 (1972); *Nature* (London), 251:443–444 (1974); *Proceedings of the National Academy of Sciences* (USA), 71:84–88 (1974). These cells are routinely cultured in RPMI 1640 supplemented with 50 µg/ml gentamicin sulfate and 10% fetal calf serum.

The reaction is terminated by filtration through a glass fiber filter harvesting system using filters previously soaked for 20 minutes in 0.1% polyethylenimine. Specific binding of labeled substance P is determined in the presence of 20 nM unlabeled ligand.

NK-2 Receptor Binding Assay

The CHO-hNK-2R cells, a CHO-derived cell line transformed with the human NK-2 receptor, expressing about 400,000 such receptors per cell, are grown in 75 cm² flasks or roller bottles in minimal essential medium (alpha modification) with 10% fetal bovine serum. The gene sequence of the human NK-2 receptor is given in N. P. Gerard, et al., *Journal of Biological Chemistry*, 265:20455–20462 (1990).

For preparation of membranes, 30 confluent roller bottle cultures are dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells are pooled and centrifuged at 1,000 RPM for 10 minutes in a clinical centrifuge. Membranes are prepared by homogenization of the cell pellets in 300 ml 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets are washed once using the above procedure. and the final pellets are resuspended in 100–120 ml 50 mM Tris buffer, pH 7.4, and 4 ml aliquots stored frozen at −70° C. The protein concentration of this preparation is 2 mg/ml.

For the receptor binding assay, one 4-ml aliquot of the CHO-hNK-2R membrane preparation is suspended in 40 ml of assay buffer containing 50 mM Tris, pH 7.4, 3 mM manganese chloride, 0.02% bovine serum albumin (BSA) and 4 μg/ml chymostatin. A 200 μl volume of the homogenate (40 μg protein) is used per sample. The radioactive ligand is [$_{125}$I]iodohistidyl-neurokinin A (New England Nuclear, NEX-252), 2200 Ci/mmol. The ligand is prepared in assay buffer at 20 nCi per 100 μl; the final concentration in the assay is 20 pM. Non-specific binding is determined using 1 μM eledoisin. Ten concentrations of eledoisin from 0.1 to 1000 nM are used for a standard concentration-response curve.

All samples and standards are added to the incubation in 10 μl dimethylsulfoxide (DMSO) for screening (single dose) or in 5 μl DMSO for IC$_{50}$ determinations. The order of additions for incubation is 190 or 195 μl assay buffer, 200 μl homogenate, 10 or 5 μl sample in DMSO, 100 μl radioactive ligand. The samples are incubated 1 hr at room temperature and then filtered on a 48 well Brandel cell harvester through GF/B filters which have been presoaked for two hours in 50 mM Tris buffer, pH 7.7, containing 0.5% BSA. The filter is washed 3 times with approximately 3 ml of cold 50 mM Tris buffer, pH 7.7. The filter circles are then punched into 12×75 mm polystyrene tubes and counted in a gamma counter.

Utility of the compounds described herein is illustrated by activity in at least one of the above assays.

Since the compounds of Formula I are effective tachykinin receptor antagonists, these compounds are of value in the treatment of a wide variety of clinical conditions which can be due to an excess of tachykinin. Thus, the invention provides methods for the treatment or prevention of a physiological disorder associated with an excess of tachykinins, which method comprises administering to a mammal in need of said treatment an effective amount of a compound of Formula I or a pharmaceutically acceptable salt, solvate or prodrug thereof. The term "physiological disorder associated with an excess of tachykinins" encompasses those disorders associated with an inappropriate stimulation of tachykinin receptors, regardless of the actual amount of tachykinin present in the locale.

These physiological disorders may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease; allergies such as eczema and rhinitis; hypersensitivity disorders such as poison ivy; ophthalmic diseases such as conjunctivitis, vernal conjunctivitis, and the like; cutaneous diseases such as psoriasis, contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues, gastrointestinal disorders or diseases associated with the neuronal control of viscera such as ulcerative coliris, Crohn's disease and irritable bowel syndrome; disorders of bladder function such as bladder detrusor hyper-reflexia and incontinence; disorders of blood flow caused by vasodilation and vasospastic diseases such as angina, migraine, and Reynaud's disease; and pain or nociception, for example, that attributable to or associated with any of the foregoing conditions, especially the transmission of pain in migraine. For example the compounds of Formula I may suitably be used in the treatment of disorders of the central nervous system such as anxiety, psychosis, and schizophrenia; neurodegenerative disorders such as Alzheimer's disease and Down's syndrome; respiratory diseases such as bronchospasm and asthma; inflammatory diseases such as artritis, inflammatory bowel disease; adverse immunological disorders such as rejection of transplanted tissues; gastrointestinal disorders and diseases such as disorders associated with the neuronal control of viscera such as ulcerative coliris, Crohn's disease and irritable bowel syndrome; incontinence; disorders of blood flow caused by vasodilation; and pain or nociception, for example, that attributable to or associated with any of the foregoing conditions or the transmission of pain in migraine.

For example, NK-1 antagonists are most especially preferred in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opiod-resistant pain, visceral pain, surgical pain, bone injury pain, pain during labor and delivery, pain resulting from burns, post partum pain, angina pain, and genitourinary tract-related pain including cystitis.

In addition to pain, NK-1 antagonists are especially preferred in the treatment and prevention of urinary incontinence; motility disorders of the gastrointestinal tract, such as irritable bowel syndrome; acute and chronic obstructive airway diseases, such as bronchospasm, bronchopneumonia, asthma, and adult respiratory distress syndrome; inflammatory conditions, such as arthritis inflammatory bowel disease, ulcerative coliris, Crohn's disease, neurogenic inflammation, allergies, rhinitis, cough, urticaria, conjunctivitis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are especially preferred in the treatment of urinary incontinence, bronchospasm, asthma, adult respiratory distress syndrome, motility disorders of the gastrointestinal tract, such as irritable bowel syndrome, and pain.

We claim:

1. A method for the treatment or prevention of a physiological disorder associated with an excess of tachykinins, which method comprises administering to a mammal in need of said treatment an effective amount of a compound of Formula I

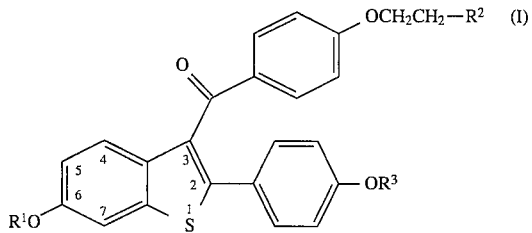

wherein $R^1$ and $R^3$ are independently hydrogen,

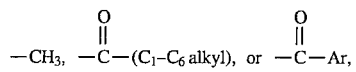

wherein Ar is optionally substituted phenyl;

$R^2$ is selected from the group consisting of pyrrolidine, hexamthylenemino, and piperidino; or a pharmaceutically acceptable salt of solvate thereof.

2. The method of claim 1 wherein said compound is the hydrochloride salt thereof.

3. The method of claim 1 wherein said administration is prophylactic.

4. The method of claim 1 wherein said compound is

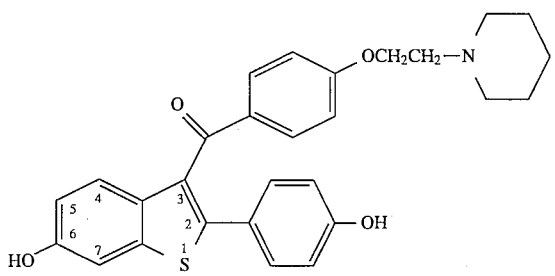

or its hydrochloride salt.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Phe Xaa Gly Leu Met
    1               5

( 2 ) INFORMATION FOR SEQ ID NO:2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Arg Pro Lys Pro Gln Gln Phe Phe Gly Leu Met
    1                  5                         10

( 2 ) INFORMATION FOR SEQ ID NO:3:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

His Lys Thr Asp Ser Phe Val Gly Leu Met
    1               5                   10

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Asp Met His Asp Phe Phe Val Gly Leu Met
    1               5                   10